United States Patent [19]
Petrofsky

[11] Patent Number: 5,974,342
[45] Date of Patent: Oct. 26, 1999

[54] ELECTRICAL STIMULATION THERAPY METHOD AND APPARATUS

[75] Inventor: Steven H. Petrofsky, Dayton, Ohio

[73] Assignee: Electrologic of America, Inc., Dayton, Ohio

[21] Appl. No.: 09/170,751

[22] Filed: Oct. 13, 1998

Related U.S. Application Data

[60] Provisional application No. 60/062,154, Oct. 16, 1997, abandoned.

[51] Int. Cl.⁶ ...................................................... A61N 1/36
[52] U.S. Cl. ............................................................ 607/50
[58] Field of Search ................................. 607/50, 63, 72, 607/148

[56] References Cited

U.S. PATENT DOCUMENTS

| 4,580,570 | 4/1986 | Sarrell et al. ............................. 607/63 |
| 4,895,154 | 1/1990 | Bartelt et al. ............................. 607/50 |

*Primary Examiner*—William E. Kamm
*Attorney, Agent, or Firm*—Jacox, Meckstroth & Jenkins

[57] ABSTRACT

A method and apparatus are provided for a therapy current to be applied for treatment for increasing circulation and allowing for rapid healing of injured tissue, tendon, or muscle areas. The apparatus applies a therapeutic current to the area of injury with little or no discomfort using three or four associated channels of electrical stimulation with a novel waveform and channel interaction.

20 Claims, 6 Drawing Sheets

Therapy Treatment Wrap

ELECTRICAL STIMULATION THERAPY METHOD AND APPARATUS

This application is based on U.S. Provisional Application No. 60/062,154 filed Oct. 16, 1997 and now abandoned.

BACKGROUND OF THE INVENTION

When animals are affected by conditions or ailments that affect circulation or the ability to contract muscle, there are not many options available for the therapy necessary to decrease healing time. Among these ailments are post-surgical edema, muscle aches and pains, tendon injuries, bone healing and wound healing. Specifically in equine, bucked shins, bowed tendons, laminitis and other leg ailments are common. Many of the same problems occur in humans.

Some devices have been developed that attempt to increase circulation through the use of magnetics, laser light, infrared light and other forms of non-invasive methods. While many animals do not have traumatic reactions to the therapy as they would with more invasive procedures, the safety and efficacy of these products have not been proven.

Functional Electrical Stimulation (FES) is an effective treatment for muscle and circulation disorders and ailments in humans as well as animals. Unfortunately, whereas humans tend to rationalize the immediate discomfort produced by FES in favor of the overall long term benefits, non-human animals are less accommodating. When the sensation of the treatment is introduced, most animals, especially horses, tend to react in unfavorable ways, such as kicking and biting, in an attempt to cause the sensation to cease. The challenge has been to produce a technique that employs FES where the animal will tolerate the higher levels of stimulation necessary to treat effectively the affected area.

When a person sustains a spinal cord injury or stroke, the body is not very good at things like circulation and wound healing. It takes the help of sophisticated technology to replace these functions that were once taken for granted. Surprisingly, there are many similarities to the horse limb. While it is designed for long periods of standing, the horse limb does not deal well with blood circulation. Because of this, a horse is more prone to injury and other ailments in the legs. When an injury occurs, it is difficult to heal.

SUMMARY OF THE INVENTION

The method and apparatus or device of the present invention has been developed to not only treat an injury effectively, but to prevent injury as well. While the method and apparatus described herein is in connection with a large animal such as a horse, it is to be understood that the method and apparatus also apply to a human. The device of the invention is an offshoot of therapy developed for the human spinal cord injury, for example, as disclosed in U.S. Pat. No. 5,048,522 issued to the applicant herein. The device of the invention uses a unique waveform in combination with a special ramping pattern to produce FES at levels where it does not excite the animal unnecessarily, but applies FES at heightened levels.

Unlike magnets or laser therapy, the device of the invention acts with the tissue at the surface as well as deep in the muscle. The device is appropriate for a wide range of injuries, from injuries that lie close to the surface like an open wound, bowed tendon, bucked shin, torn check ligament, curb, inflamed sesamoid or suspensory ligament, splint, injection-site abscess, inflammation from a superficial wound and other soft tissue injuries. Deeper injuries like a deep muscle tear, can also be treated. Unlike many other therapies available, the device of the invention may be used both for chronic as well as acute injuries.

In addition to treating injuries, regular sessions of the device of the invention may be used as a therapeutic treatment, both as general care and before or after competition. For example, if you increase blood flow without distressing the injured tissue, you can speed up healing. The device of the invention does this by recruiting the natural nervous system of the horse or other animal.

When trauma strikes, the most visible symptom of injury is swelling. Vessels damaged by trauma injury leak fluid into the surrounding tissue, causing swelling. Regardless of the injury type, this process, though simplified greatly, is repeated for each injury. Obviously, in the case of open wounds, the danger of bacteria and infection also exists. Early treatment should include cold compresses and/or suturing if necessary, to constrict damaged vessels and minimize fluid loss. Once the injury has been stabilized, the use of the device of the present invention can begin almost immediately. The most dramatic use of this device is on a soft tissue injury where there is swelling. Unlike lasers or magnets, you can see the tissue contract and feel the muscle become warm as the blood is pumped to and around the injury.

In general, injuries that are treated during the acute phase of the injury are easier to treat, have a greater likelihood of returning to full function, and respond quickly. Moreover, there is less of a chance that rigid, inflexible scar tissue will form in and around the injury. An animal's body is designed as a very complex communication network, with the brain and nerves constantly sending signals back and forth to each other using small electrical impulses. When a muscle is at rest, the level of activity in the muscle tissue slows down, conserving energy. When an injury occurs, the cells in the injured area receive signals through the nervous system from the brain to first ward off infection and next, to heal. The healing is a process of removing fluid, cell debris and importing proteins to rebuild the cells. This process, though efficient, is slow. The device of the invention helps speed the process by recruiting the nerves locally, increasing the blood flow through increased capillary action and ultimately increasing the activity of exporting the fluid and cell debris and importing the proteins to the injured area. This is accomplished in a non-invasive manner using the device and a set of six surface skin electrodes.

The device of a preferred form of the invention uses a microprocessor and a gate array to produce an electronically generated complex set of waveforms applied across the six surface electrodes. As the electronic pulses enter through the skin, nerves are recruited to act upon the tissue. The deep penetration of the low discomfort electrical biphasic current causes an immediate measurable increase in the tissue circulation unlike animal laser products or magnetic blankets. TENS devices have tried for this modality but have been seen to be too painful for the animal or have startled the animal into an uncontrollable frenzy.

Unlike other devices that only attempt to work over a local area, the device of the present invention uses a cross-communication model with tri-wave technology. The signal is crossed from one side of the injury to the other and back again. The two channels using four surface electrodes placed across the injury site are ramped together to increase slowly the level of electrical stimulation to allow the animal to accommodate to the treatment while the third channel across the injury manages the flow of signals to keep the treatment local. The result is a concentration and acceleration of blood flow, fluid expulsion and protein importation. An alternate mode for taking advantage of a four channel electrical stimulus is used for increasing circulation in two legs at the same time. This takes advantage of the waveform and incorporates the connection of two treatment pads of the invention. One treatment pad per leg being connected in the x-pattern of the treatment pad channels. This mode also uses a fourth stimulus channel.

One of the typical applications of the device is for Equine use. When a horse sustains an injury, it is important to minimize swelling as much as possible. The device uses surface electrode delivery systems incorporating six surface electrodes correctly placed for use on the shin area by a primary wrap. The wrap is tightened around the injured shin area after liberal amounts of conductive gel have been applied to the surface electrodes. The device is set for at least 45–60 minutes of therapy. Once it is started, the level of stimulation is gradually brought up to a level when the horse reacts negatively. As the horse adjusts to the sensation and the therapy works to anesthetize the injury, the level is increased slightly. The level will be increased a few points every 1–2 minutes. The level is continued to be increased for approximately 10 minutes. This level will remain for the remaining 45–60 minute session. Once the session is complete, the electrode wrap is removed from the injured area.

DETAILED DESCRIPTION OF THE PREFERRED EMBODIMENTS

Figure 1:
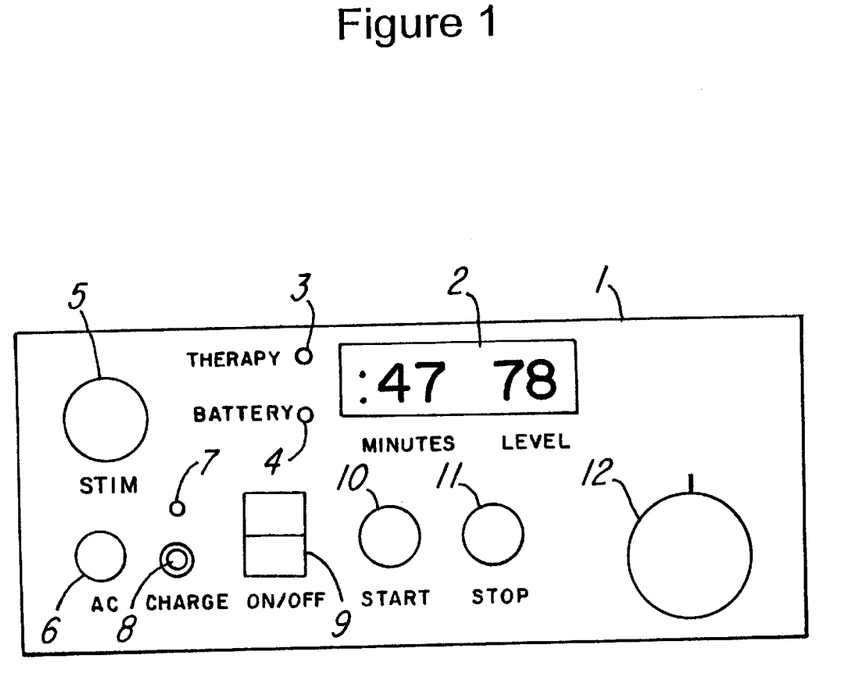
FIG. 1 is an elevation view of a front control panel of an electrical stimulating device constructed to operate in accordance with the invention.

Referring to FIG. 1 which shows the operational controls for a device constructed in accordance with the invention, a front panel 1 contains an 8 character, one line LCD display 2 for indicating to the user of the device the session time and the therapy level being administered. Two LEDs are used to display when a therapy current is being applied by energizing LED 3 and/or by showing a low battery charge condition by energizing LED 4. A waterproof connector 5 allows connection to a therapy wrap which contains six surface electrodes (described later). The invention is powered by a rechargeable lead acid battery for animal safety during treatment in the field or barn. An optional AC medical grade CSA, IEC, UL-544 rated external power supply can be connected to power the system safely through the waterproof connector 6. During normal use, the battery will discharge within a few hours of therapy. An external battery charger is attached through connector 8 which disconnects the battery power from the device and energizes the charge LED 7. This is to protect the animal from potential risk currents from the AC while using the battery charger. Power supply to the device is controlled by a main power rocker switch 9.

When the initial power is turned on, a set of microprocessor controlled diagnostics test the integrity of the electronics and the main program software. If the power on test passes, the user will be allowed to continue. If not, the unit will not allow a therapy session until the unit is repaired. During normal power on operations, the user will adjust the amount of session time to be conducted between 16–60 minutes using the level adjustment encoder knob 12. When set, the user will push the "START" button 10 to initiate a session. For the animal safety, the therapy current is always initialized to "0". A maximum user setting is 100. The user will then adjust slowly the level encoder knob 12 to a level of current at which the animal shows a small amount of irritation from the stimulus. The knob 12 is then backed down 2–3 levels for a 1–2 minute time period and then increased in level again. This easing up on the therapy level will be conducted for 10 minutes. This allows for best accommodation to the therapy and the analgesic affects of the waveform. The remainder of the session will be conducted at that level of current. The therapy session will terminate by the session set time having expired, a low battery charge condition, or by the intentional depressing of the "STOP" button 11. The system will display three different termination messages on the LCD module.

Figure 2:
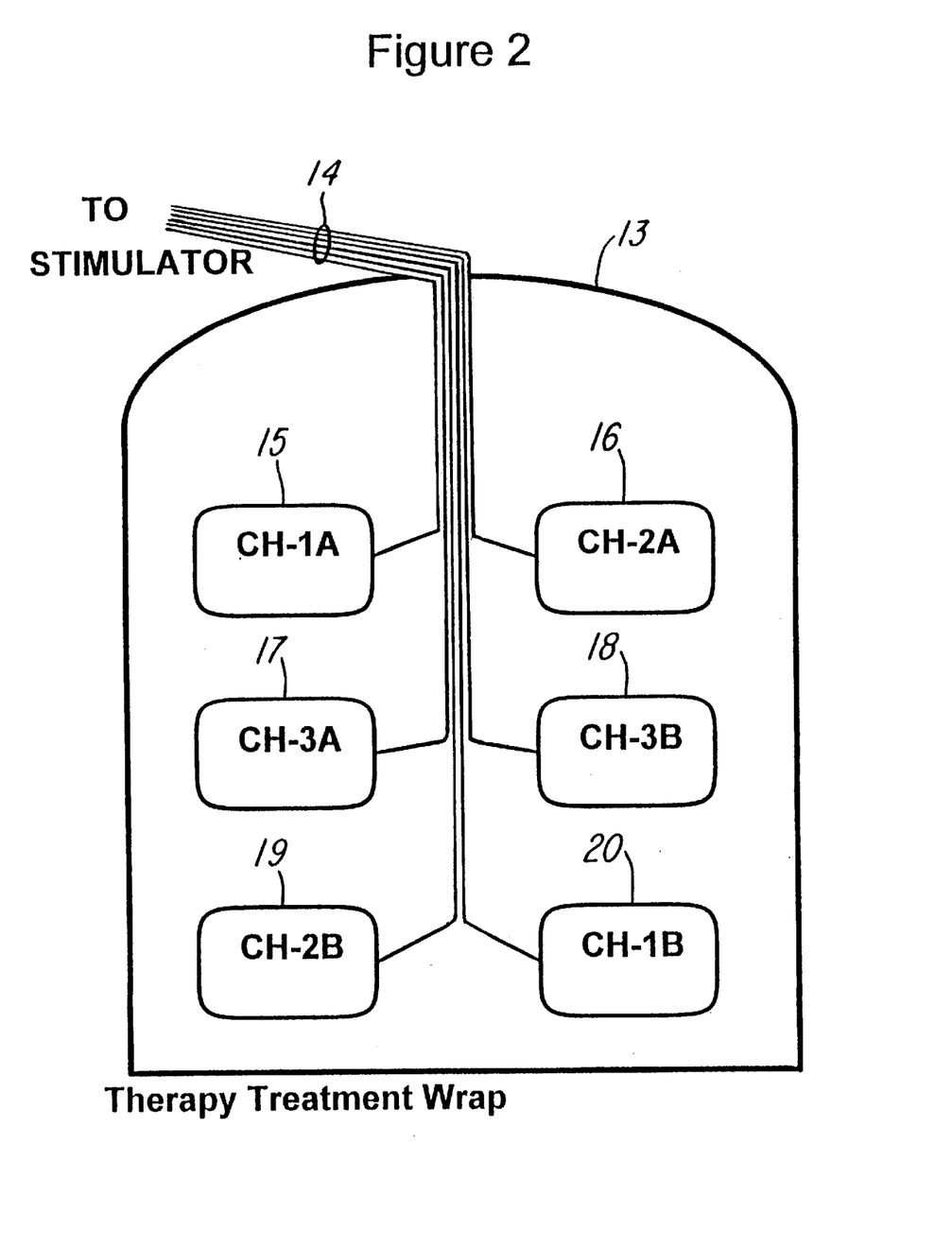
FIG. 2 is a front view of a therapy treatment wrap containing six electrodes for applying three pairs of therapy current to an animal across and through an injury.

Referring to FIG. 2, a typical therapy treatment wrap 13, in the form of a fabric or a flat pad, contains six surface electrodes 15–20 placed in the proper orientation to supply the therapy current across and through an injured area with proper phasing of the signals. A cable 14 having a length depending upon the animal and application, is connected to the portable therapy device such as the equine application mentioned earlier. The surface electrodes are phased to allow for therapy currents to pass diagonally across the injured area using currents from channels one electrodes 15 & 20 and channel two electrodes 16 & 19. Additional current flow across the injured area is supplied by channel three electrodes 17 & 18 at a different time sequence than channels one and two.

Figure 3:
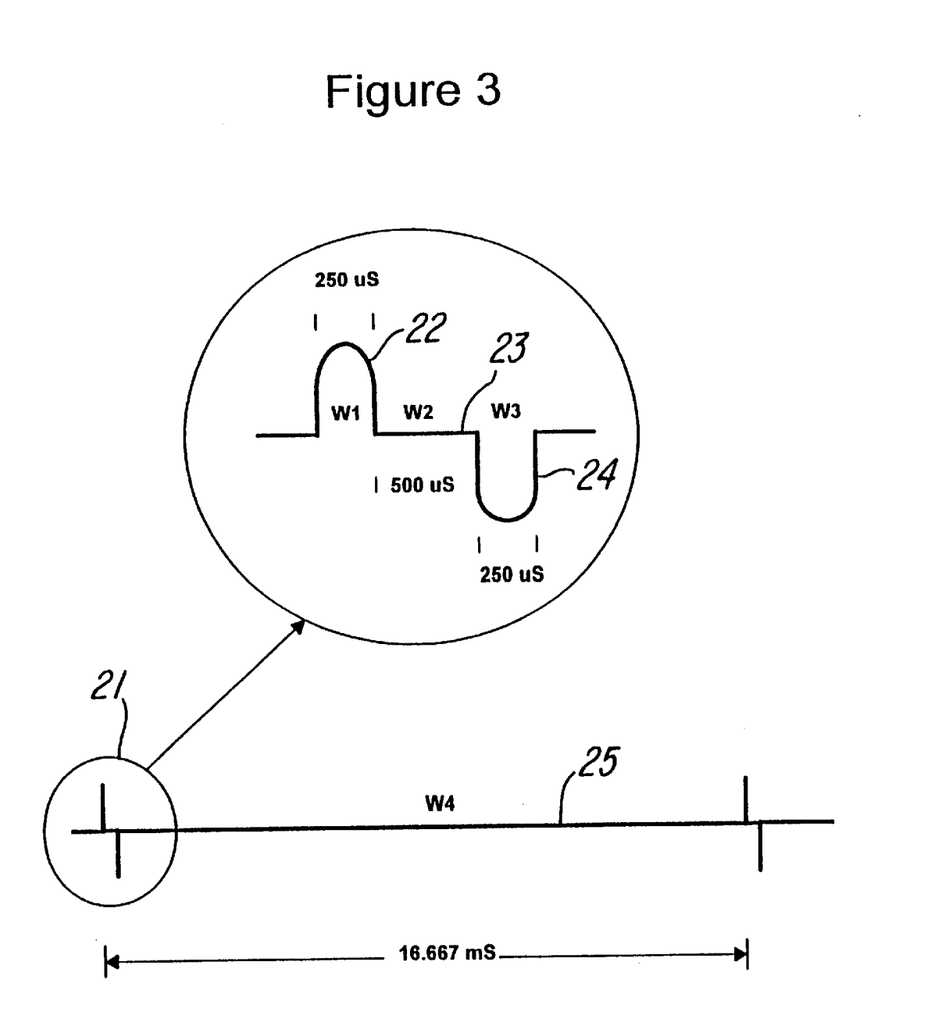
FIG. 3 illustrates a Biphasic waveform applied by computer control independently through the electrode pairs and showing the wave shape and repetition rate.

FIG. 3 shows the therapy waveform applied to the surface electrodes. This waveform has a delayed inter-phase timing and is a constant voltage or current balanced charge biphasic type. The waveform can be either a sinusoid or a square wave as long as the stimulus parameters are adhered to. In the various applications, the output voltage maximums will be in the range of 1 to 75 volts, or as shown, into a 500 ohm load of 1 to 150 milliamps. The waveform 21 consists of a positive phase 22 being 100–300 microseconds, an interphase delay 23 of 200–750 microseconds, and a negative phase 24 of 100–300 microseconds. Typical applications, such as an equine application, use a 250, 500, and 250 microsecond set of parameters as shown in FIG. 3. This delayed inter-phase waveform 25 is generated at a rate of 40–80 times per second. A typical use of this waveform is 60 repetitions per second or every 16,667 milliseconds.

In order to avoid startling an animal but to apply the therapy current in heavy enough doses to increase circulation significantly, a special profile relationship (FIG. 4) of two independent but related ramping profiles is used. The ramping profiles for channels one and two which apply the therapy current across the injured area diagonally, are shown at 26. The ramping profile for channel three which applies its current directly across the injured area after being setup and anesthetized by channels one and two, is shown at 27. All channel profiles maintain a four second period 34 to be repeated over and over until the session is complete. The profiles ramp up to the set level prescribed by the user during the application on the animal to the tolerable level using the level encoder knob 12 described earlier.

Figure 4:
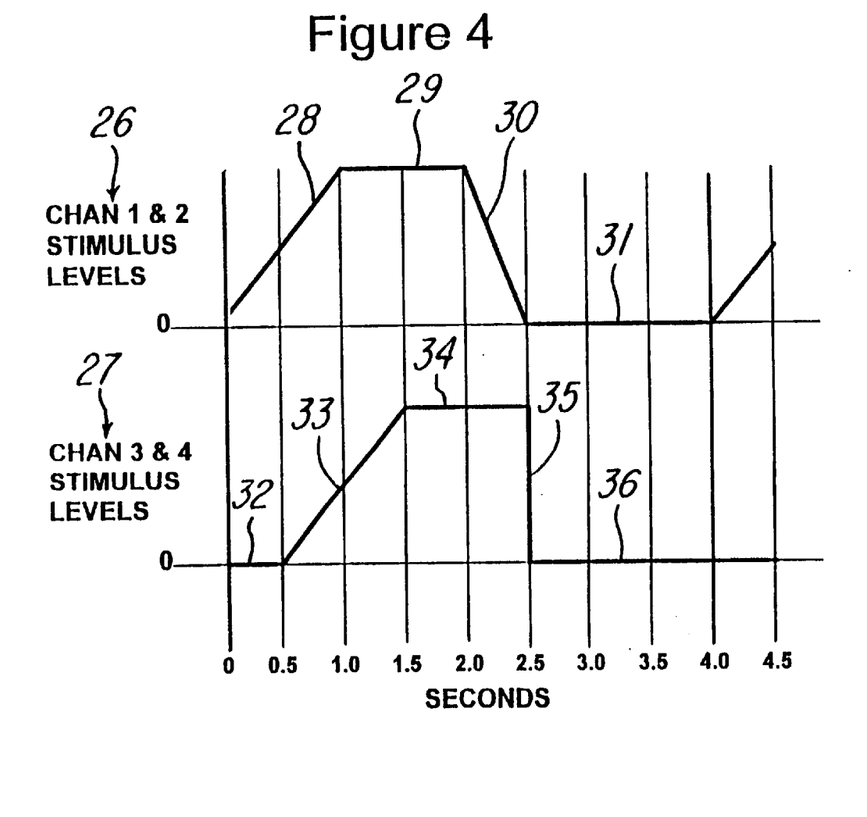
FIG. 4 illustrates the ramping relationship between the three profiles of therapy currents for channels 1, 2, 3, and 4.

A 2.0–8.0 second period consists of channel one and two ramping up at 28 for a 0.5–2.0 seconds elapsed time to the user set maximum. Channels one and two are held at the level 29 for a 0.5–2.0 seconds time period and then ramp down at 30 to a zero level during the next 0.25–1.0 seconds. During the next 0.75–3.0 seconds, the current on channels one and two at 31 will remain at zero (rest time). After a 0.25–1.0 seconds delay 32 from the start of channel one and two ramps, channel three will ramp up at 33 during a 0.5–2.0 second period. Channel three is held at the maximum programmed level 34 for 0.5–2.0 seconds even during the ramp down at 30 on channels one and two. Channel three then drops at 35 to zero with no ramp down to also rest at zero at 36 for 0.75–3.0 seconds with channels one and two. The repeating period is between 2.0 seconds and 8.0 seconds depending on the treatment modality. As shown, the large equine animal application uses 4 seconds.

Figure 5A:
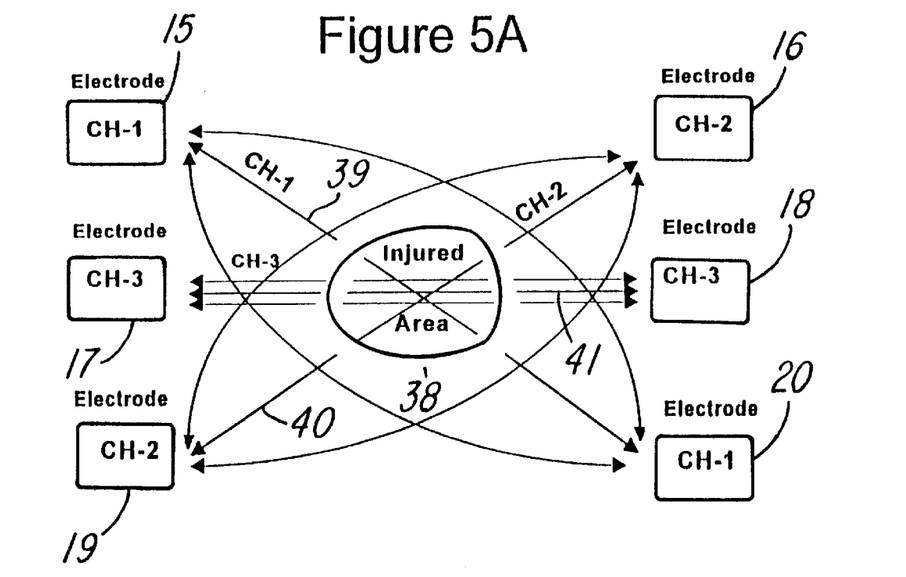
FIG. 5A is an expanded diagram showing the relationship between the three therapy electrical current pairs during operation of the system, with the injured area entirely encompassed by the current.

FIG. 5A shows how the currents are applied by the electrodes to the injured area in accordance with the invention. An injured area 38 is surrounded by the six surface electrodes. Channel one electrodes 15 and 20 apply the therapy current 39 across and through the injured area 38 according to the current density field. The highest currents pass directly between the electrodes, and the field diminishes the further away for the direct path. Channel two applies current 40 in a similar manner in the opposite diagonal using electrodes 16 and 19 as shown. By phasing the currents 41 in channel three using electrodes 17 and 18 with the diagonal currents of channels one and two, a significant increase in muscle and/or skin capillary blood flow action occurs.

Figure 5B:
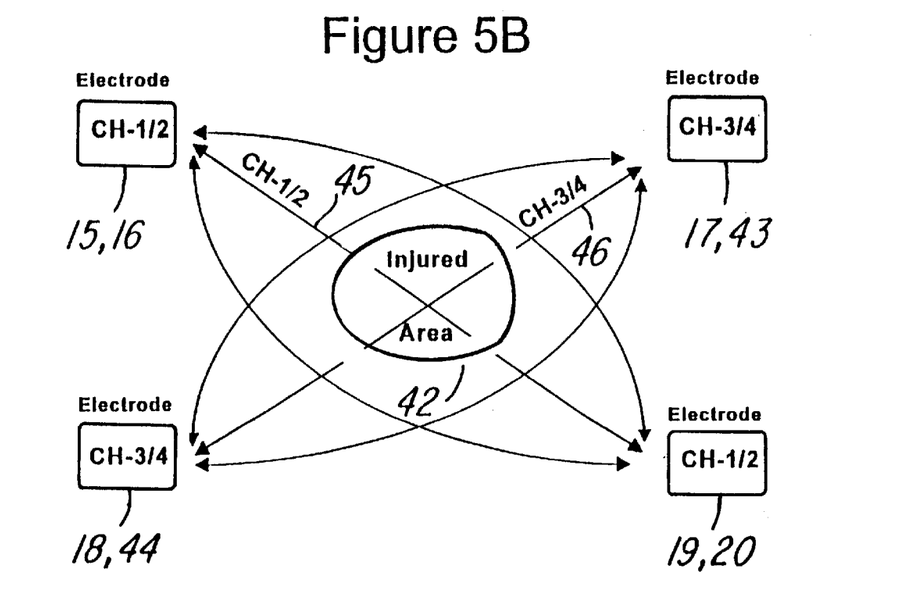
FIG. 5B is a diagram similar to FIG. 5A and showing an alternate mode using two treatment pads and four channels of electrical stimulation for distribution across two injured areas of the body at the same time.

FIG. 5B shows how the currents are applied by the electrodes to the injured area in accordance with an alternate usage. An injured area 42 on an animal is surrounded by two sets of four surface electrodes. As shown, channel one or two use electrodes 15 and 20 or 16 and 19 to apply the therapy current 45 across and through the injured area 42 according to the current density field. The highest currents pass directly between the electrodes, and the field diminishes the further away from the direct path. Channel three or four apply current 46 in a similar manner in the opposite diagonal using electrodes 17 and 18 or 43 and 44. By phasing the currents in the diagonal channels, a significant increase in muscle and/or skin capillary blood flow action occurs.

Figure 6:
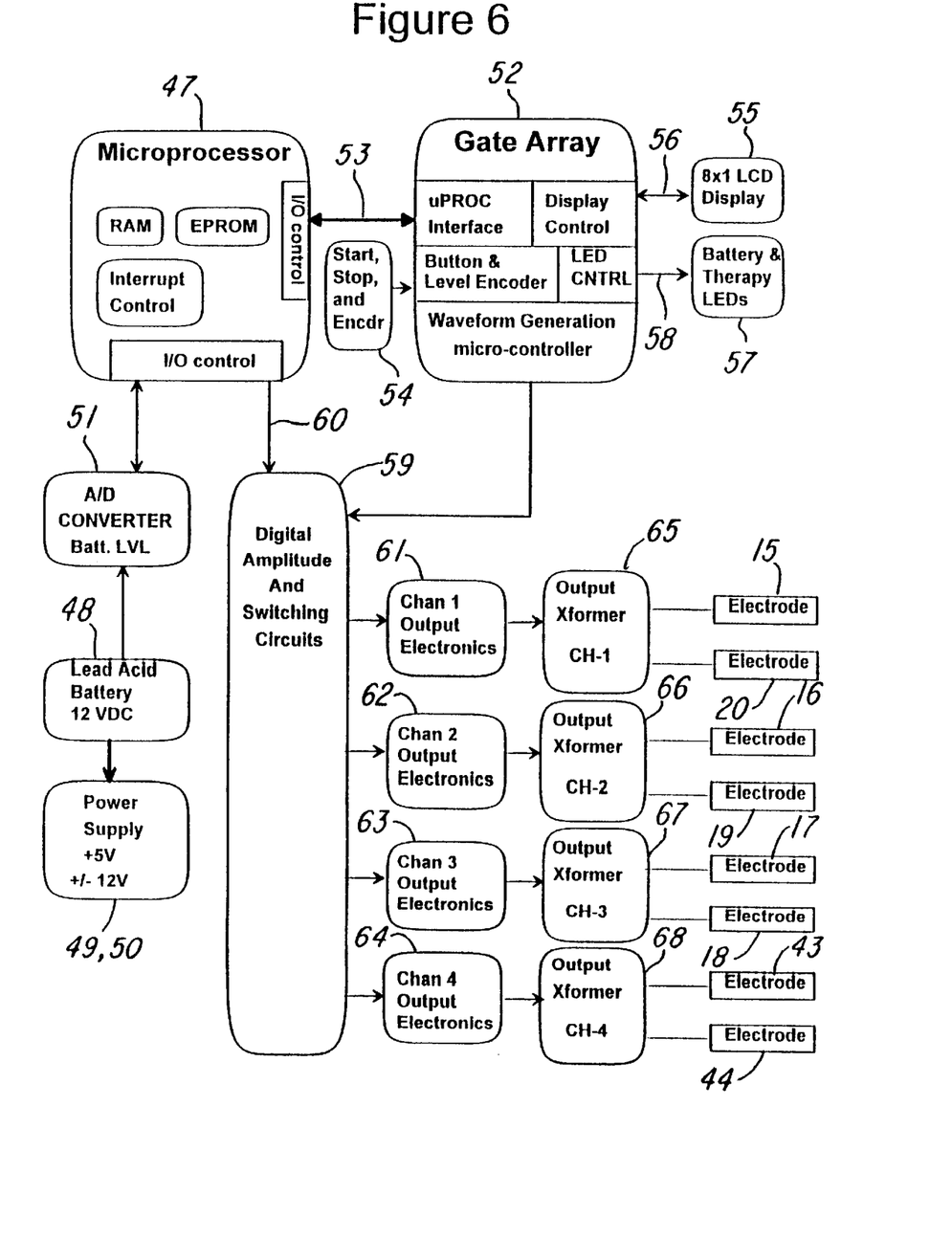
FIG. 6 is an electrical block diagram of an electrical stimulating device constructed for operation in accordance with the invention.

FIG. 6 illustrates a special purpose computer controlled electrical stimulator constructed in accordance with the invention. A Motorola MC68HC705C9AFN 8 bit microprocessor and associated circuitry 47 control this application. The stimulator or therapy device is normally powered by a 1.2 amp lead acid rechargeable battery 48 which connects to a power converter circuitry 49 through a fuse and power switch 50. The device can also be powered externally by a special medical rated power supply. The microprocessor monitors the battery level by conditioner circuits 51 and a serial 8 bit analog-to-digital converter produced by National Semiconductor. The converter is interfaced to the microprocessor using 4 I/O programmable bits.

The majority of digital circuitry contained in this application and the high speed data control is accomplished by a Xilinx XC3042 field programmable gate array 52 containing 4200 gates. The gate array is programmed to contain the digital circuitry for the microprocessor interface, the LCD display interface, the panel button interface, the gray code level encoder interface, the battery and therapy LED light control interface, the complex waveform generator and microcontroller, and an interrupt controller. The communication between the gate array and the microprocessor is accomplished over a custom bi-directional programmable data bus 53 with its associated bus control signals. The gate array internal circuitry contains pull-up resisters for directly connecting the START, STOP, and Level Encoder switch devices 54. The 8 character by 1 line super twist LCD with LED backlight alpha numeric module 55 is connected by a custom bi-directional data bus 56 to the gate array programmed LCD controller circuitry. The battery and therapy LEDs 57 are controlled by the gate array interface 58.

The four channels of special purpose electrical stimulation which generate the therapy currents applied to the animal, are developed by a high speed real-time waveform generator and controller contained in the gate array. The waveform is applied to an analog switching matrix 59 under the control of the gate array to develop the positive phase 22, the delay phase 23, and the negative phase 24 portions of the waveform. The dwell time between the output waveforms is also controlled by the gate array controller and the analog switch matrix. The output of the switching matrix 59 is fed to four digital potentiometers for adjusting the profile levels of therapy current under the control of the microprocessor through an I/O programmable interface 60. The microprocessor will control the profiles of the therapy current through a real-time clock interrupt occurring every 0.1 seconds.

The four digital potentiometers with bipolar outputs feed the channel 1, 2, 3, and 4 with independent electronics and control circuitry 61, 62, 63, and 64. For the animal's safety, isolation transformers 65–68 are used to connect directly to the electrodes. These transformers 65–68 guarantee that therapy currents can not travel from one therapy channel to the other, thus keeping accidental current paths away from the heart and other vital organs. The independent transformers also act in the circuit to step-up the therapy voltage to the desired level. As mentioned, the output of transformer 65 for channel one connects via the stimulus cable to the surface electrodes 15 and 20. Likewise transformers 66, 67, and 68 connect channels two, three and four to electrodes 16 & 19, 17 & 18, and 43 & 44, respectively.

I claim:

1. A method of providing electric stimulation therapy to an injured area on a living body, comprising the steps of:

generating three stimulus channels of constant voltage or current biphasic electrical stimulation including a 100 to 300 microsecond positive phase, a 200 to 750 microsecond inter-phase and a 100 to 300 microsecond negative phase occurring once every 12.5 to 25 milliseconds;

ramping the currents of two stimulus channels from zero up to a predetermined amplitude to obtain a treatment level for a first time period, holding the treatment level for a predetermined time period, ramping the currents down to zero within a predetermined time period, and holding the currents at zero for a predetermined time period;

holding the current of the third stimulus channel at substantially zero for a predetermined time period, ramping the third channel current up to a predetermined treatment level within a predetermined time period and out of phase with the ramping of the currents of the two stimulus channels, holding the treatment level for a predetermined time period, and then dropping the current level to substantially zero and holding the current level for a predetermined time period;

repeating the above stimulus profiles several times per minute for a treatment session; and applying the above stimulus profiles to the injured area of the body in a crossing X-pattern using a plurality of electrodes spaced around the injured area.

2. The method of claim 1 wherein the currents of the third stimulus channel are applied on opposite sides of the injured area by two of the electrodes.

3. The method of claim 1 and including the step of applying an electrical stimulation current of 1–75 milliamps to a muscle in the injured area to increase the blood circulation and muscle stimulation for reducing the healing duration.

4. The method of claim 1 and including the step of stimulating a muscle in the injured area with an electrical current of 40–150 milliamps to reverse disuse atrophy in the muscle.

5. The method of claim 1 and including the step of stimulating a tendon with a deep penetrating electrical stimulation current of 1–75 milliamps to increase the interior blood circulation in the injured area for reducing the healing duration.

6. The method of claim 1 and including the step of stimulating soft tissue within the injured area with an electrical stimulation current of 1–75 milliamps to increase the interior blood circulation to the injured area for reducing the healing duration.

7. A method of providing electric stimulation therapy to body tissue, muscle and tendon, comprising the steps of:

generating three stimulus channels of constant voltage or current biphasic electrical stimulation including a 100 to 300 microsecond positive phase, a 200 to 750 microsecond inter-phase and a 100 to 300 microsecond negative phase occurring once every 12.5 to 25 milliseconds while maintaining a phase to inter-phase period ratio of about 1:2;

ramping the currents of two stimulus channels from zero up to a predetermined amplitude to obtain a treatment level for a first time period between 0.5 and 2.0 seconds, holding that level for a period between 0.5 and 2.0 seconds, ramping the currents down to zero within a time period between 0.25 and 1.0 seconds, and holding the currents at zero for a time period between 0.75 and 3.0 seconds;

holding the current of the third stimulus channel at zero for a time period between 0.25 and 1.0 seconds, ramping the third channel current up to a predetermined treatment level within a time period between 0.5 and 2.0 seconds, holding that desired treatment level for a period between 0.5–2.0 seconds, and then dropping and holding the current level at zero for a time period between 0.75 and 3.0 seconds;

repeating the above stimulus profiles every 2 to 8 seconds for a treatment session between 1 and 60 minutes; and applying the above treatment amplitude profiles to an injured area of the body using a plurality of electrodes spaced around the injured area.

8. The method of claim 7 wherein the currents of the two stimulus channels are applied by the electrodes in an X-pattern crossing the injured area.

9. The method of claim 7 wherein the currents of the third stimulus channel are applied on opposite sides of the injured area by two of the electrodes.

10. The method of claim 7 and including the step of applying an electrical stimulation current of 1–75 milliamps to a muscle in the injured area to increase the blood circulation and muscle stimulation for reducing the healing duration.

11. The method of claim 7 and including the step of stimulating a muscle in the injured area with an electrical current of 40–150 milliamps to reverse disuse atrophy in the muscle.

12. The method of claim 7 and including the step of stimulating a tendon with a deep penetrating electrical stimulation current of 1–75 milliamps to increase the interior blood circulation in the injured area for reducing the healing duration.

13. The method of claim 7 and including the step of stimulating soft tissue within the injured area with an electrical stimulation current of 1–75 milliamps to increase the interior blood circulation to the injured area for reducing the healing duration.

14. A method of providing electric stimulation therapy to body tissue, muscle and tendon comprising the steps of:

generating four stimulus channels of constant voltage or current biphasic electrical stimulation including a 100 to 300 microsecond positive phase, a 200 to 750 microsecond inter-phase, a 100 to 300 microsecond negative phase occurring once per 12.5 to 25 milliseconds while maintaining the phase to the inter-phase period ratio of 1:2;

ramping the currents of two stimulus channels to produce a 0–150 milliamp treatment level during the first 0.5–2.0 seconds, holding the level for 0.5–2.0 seconds, ramping down to zero during the next 0.25–1.0 second interval, and holding at zero for 0.75–3.0 seconds.

ramping the currents of stimulus channel three and four out of phase with channel one and two to obtain a predetermined treatment level, holding the treatment level for 0.5–2.0 seconds and then dropping to zero amplitude for 0.75–3.0 seconds; repeating the above stimulus profiles every 2.0–8.0 seconds during a 1–60 minute treatment session; and applying stimulus profiles to the injured area of the body by a plurality of electrodes spaced around the injured area.

15. The method of claim 14 wherein electrical stimulus channels one and three is applied to the injured area in a crossing X-pattern by the electrodes.

16. The method of claim 14 wherein the electrical stimulus of channels two and four are applied to the injured area in a crossing X-pattern by the electrodes.

17. The method of claim 14 and including the step of applying an electrical stimulation current of 1–75 milliamps to the injured area for increasing the blood circulation for reducing the healing duration in the injured area.

18. The method of claim 14 and including the step of applying an electrical stimulation current of 40–150 milliamps to a muscle in the injured area for reversing muscle disuse atrophy in the injured area.

19. The method of claim 14 and including the step of stimulating a tendon in the injured area with an electrical stimulation current of 1–75 milliamps to increase blood circulation to the injured area for reducing the healing duration.

20. The method of claim 14 and including the step of applying a low electrical stimulation current of 1–75 milliamps to soft tissue in the injured area to increase blood circulation to the injured area for reducing the healing duration.

* * * * *